United States Patent
Krishnaswamy et al.

(10) Patent No.: US 10,485,425 B2
(45) Date of Patent: Nov. 26, 2019

(54) APPARATUS AND METHODS FOR STRUCTURED LIGHT SCATTEROSCOPY

(71) Applicant: The Trustees of Dartmouth College, Hanover, NH (US)

(72) Inventors: Venkataramanan Krishnaswamy, Lebanon, NH (US); Brian W. Pogue, Hanover, NH (US); Keith D. Paulsen, Hanover, NH (US); Jonathan T. Elliott, West Lebanon, NH (US); David M. McClatchy, III, Hanover, NH (US)

(73) Assignee: THE TRUSTEES OF DARTMOUTH COLLEGE, Hanover, NH (US)

(*) Notice: Subject to any disclaimer, the term of this patent is extended or adjusted under 35 U.S.C. 154(b) by 466 days.

(21) Appl. No.: 15/116,808

(22) PCT Filed: Feb. 4, 2015

(86) PCT No.: PCT/US2015/014416
§ 371 (c)(1),
(2) Date: Aug. 4, 2016

(87) PCT Pub. No.: WO2015/120020
PCT Pub. Date: Aug. 13, 2015

(65) Prior Publication Data
US 2017/0164836 A1    Jun. 15, 2017

Related U.S. Application Data

(60) Provisional application No. 61/935,803, filed on Feb. 4, 2014.

(51) Int. Cl.
*A61B 5/00* (2006.01)
*G01B 11/25* (2006.01)

(52) U.S. Cl.
CPC .......... *A61B 5/0059* (2013.01); *A61B 5/4869* (2013.01); *G01B 11/2513* (2013.01); *A61B 2505/05* (2013.01)

(58) Field of Classification Search
CPC ... A61B 5/0059; A61B 5/0075; A61B 5/4869; A61B 2505/05; G01B 11/2513
See application file for complete search history.

(56) References Cited

U.S. PATENT DOCUMENTS

| 4,523,809 A | 6/1985 | Taboada et al. |
| 8,509,879 B2 * | 8/2013 | Durkin ................. A61B 5/0073 600/407 |

(Continued)

OTHER PUBLICATIONS

Bevilacqua et al. (1999) "Monte Carlo study of diffuse reflectance at source—detector separations close to one transport mean free path," J. Opt. Soc. Am. A. 16(12): 2935-2945.

(Continued)

*Primary Examiner* — Sanjay Cattungal
(74) *Attorney, Agent, or Firm* — Lathrop Gage LLP (57) ABSTRACT

A structured-light imaging system includes a structured light projector for illuminating a surface and an electronic camera configured to image the surface. An image processor receives the images and has structured light scatteroscopy (SLS) firmware with machine readable instructions that illuminate the surface with structured light having a spatial frequency of at least 0.5 mm"1, and process the images to determine a map of scattering parameters at the surface independent of absorption properties. In an embodiment, the system also has cameras configured to obtain a stereo pair of images of the surface, the image processor having 3D firmware for extracting a three dimensional model of the surface from the stereo pair of images and compensating the map for non-flat surfaces.

16 Claims, 5 Drawing Sheets

(56) References Cited

U.S. PATENT DOCUMENTS

| | | | | |
|---|---|---|---|---|
| 2006/0184043 | A1* | 8/2006 | Tromberg | A61B 5/0073 600/476 |
| 2009/0036902 | A1 | 2/2009 | DiMaio et al. | |
| 2010/0021093 | A1 | 1/2010 | Plourde et al. | |
| 2010/0160789 | A1* | 6/2010 | Dilworth | A61B 3/0025 600/476 |
| 2013/0044185 | A1* | 2/2013 | Krishnaswamy | A61B 5/7257 348/45 |
| 2015/0145966 | A1* | 5/2015 | Krieger | G06T 17/20 348/47 |
| 2016/0157723 | A1 | 6/2016 | Kanick et al. | |
| 2016/0278678 | A1* | 9/2016 | Valdes | A61B 5/14556 |

OTHER PUBLICATIONS

Calabro et al. (Feb. 9, 2012) "Improved empirical models for extraction of tissue optical properties from reflectance spectra," Proc. SPIE. 8230:82300H. pp. 1-7.

Cuccia et al. (2005) "Modulated imaging: quantitative analysis and tomography of turbid media in the spatial-frequency domain," Opt. Lett. 30(11):1354-1356.

Cuccia et al. (2009) "Quantitation and mapping of tissue optical properties using modulated imaging," J. Biomed. Op. 14(2):024012. pp. 1-13.

Gamm (Oct. 4, 2013) Quantification of Tissue Scattering Properties by Use of Fiber Optic Spectroscopy, Uitgeverij BOXPress,'s-Hertogenbosch, 138 pgs.

Gioux et al. (2009) "Three-dimensional surface profile intensity correction for spatially modulated imaging," J. Biomed. Opt. 14:034045. pp. 1-11.

Gioux et al. (2011) "First-in-human pilot study of spatial frequency domain oxygenation imaging system," J. Biomed. Opt. 16(8):086015. pp. 1-10.

Jacques et al. (2008) "Tutorial on diffuse light transport," J. Biomed. Opt. 13(4):041302. pp. 1-19.

Johnson et al. (2000) "Optical light scatter imaging of cellular and sub-cellular morphology changes in stressed rat hippocampal slices," J. Neurosci. Methods. 98:21-31.

Kanick et al. (May 1, 2012) "Scattering phase function spectrum makes reflectance spectrum measured from Intralipid phantoms and tissue sensitive to the device detection geometry," Biomed. Opt. Express. 3(5):1086-1100.

Kanick et al. (Sep. 3, 2014) "Sub-diffusive scattering parameter maps recovered using wide-field high-frequency structured light imaging," Biomedical Optics Express. 5(10):3376-3390.

Kanick et al. (May 20, 2011) "Method to quantitatively estimate wavelength-dependent scattering properties from multidiameter single fiber reflectance spectra measured in a turbid medium," Optics Letters. 36(15): 2997-2999.

Konecky et al. (2011) "Imaging scattering orientation with spatial frequency domain imaging," J. Biomed. Opt. 16(12):126001. pp. 1-8.

Krishnaswamy et al. (Nov. 6, 2014) "Structured light scatteroscopy," Journal of Biomedical Optics. 19(7):070504. pp. 1-4.

Krishnaswamy et al. (2009) "Quantitative imaging of scattering changes associated with epithelial proliferation, necrosis, and fibrosis in tumors using microsampling reflectance spectroscopy," J. Biomed. Opt. 14(1):014004. pp. 1-10.

Krishnaswamy et al. (2011) "Dark-field scanning in situ spectroscopy platform for broadband imaging of resected tissue," Opt. Lett. 36:1911-1913.

Laughney et al. (2008) "System analysis of spatial frequency domain imaging for quantitative mapping of surgically resected breast tissue," J. Biomed. Opt. 18(3):036012. pp. 1-11.

Laughney et al. (Aug. 20, 2012) "Scatter spectroscopic imaging distinguishes between breast pathologies in tissues relevant to surgical margin assessment," Clin. Cancer Res. 18(22):6315-6325.

Neil et al. (1997) "Method of obtaining optical sectioning by using structured light in a conventional microscope," Optical Society of America. 22(24):1905-1907.

Qian et al. (2010) "Dark-field light scattering imaging of living cancer cell component from birth through division using bioconjugated gold nanoprobes," J. Biomed. Opt. 15:046025. pp. 1-9.

International Search Report with Written Opinion corresponding to International Patent Application No. PCT/US2015/014416, dated May 14, 2015.

International Search Report and Written Opinion dated May 14, 2015 for International Application No. PCT/US2015/014416 (9 pages).

Carlson et al. (2017) "Enhanced scatter contrast color imaging of tissue: Methods for comparing high spatial frequency domain and cross-polarization scatter images," Proc. of SPIE. 10059.

McClatchy et al. (Mar. 2015) "High spatial frequency structured light imaging for intraoperative breast tumor margin assessment," SPIE BiOS, International Society for Optics and Photonics.

McClatchy et al. (Apr. 2015) "Molecular dyes used for surgical specimen margin orientation allow for intraoperative optical assessment during breast conserving surgery," Journal of biomedical optics. 20(4):040504-040504.

Yang et al. (2014) "Real-time absorption reduced surface fluorescence imaging," Journal of biomedical optics. 19(9):090505-090505.

* cited by examiner

APPARATUS AND METHODS FOR STRUCTURED LIGHT SCATTEROSCOPY

RELATED APPLICATIONS

This application is a 35 U.S.C. § 371 filing of International Application No. PCT/US2015/014416, filed 4 Feb. 2015, which claims priority to U.S. Provisional Patent Application 61/935,803 filed on 4 Feb. 2014, the disclosure is incorporated in its entirety herein.

FIELD

The present application relates to the fields of imaging and automatic classification of biological tissues. In particular, the present application relates to using structured light to image, scan, and/or identify biological tissues.

BACKGROUND

Many tumors and other lesions superficially resemble the parent tissues from which they arise. When such tumors are treated surgically, it has been found desirable to use various devices, such as surgical microscopes and fluorescent imaging, to help a surgeon discriminate between lesions and surrounding tissues because complete removal is associated with improved patient survival, while removal of excessive normal tissue is associated with increased morbidity.

Conventional imaging systems that are widely employed in clinical settings today, including the state-of-the-art stereoscopic high-definition microscopes, are mainly sensitive to absorption-based contrast and hence are not capable of imaging subtle morphology changes in or near real-time. Conventional microscopes often rely on staining procedures that typically require days to complete, preventing use of these techniques for immediate decision-making while incisions of a patient remain open in an operating room.

It is known that, for certain diseases including some malignant and benign tumors, disease onset and progression alters tissue morphology at the cellular and subcellular levels from normal morphology. These subtle changes in morphology cause changes in light scattering and absorption that can be used as a robust contrast mechanism for early disease diagnosis and tracking.

Localized scatter imaging using single-fiber illumination or confocal optics has been shown to be effective in detecting subtle morphology changes associated with pathologically distinct tissue types and in detecting remaining malignant tissue at surgical margins during cancer surgery, mainly because of its ability to enhance contrast between normal (or benign) and malignant tissue based on the intrinsic sensitivity of scatter to underlying microscopic tissue structure. However, one of the key limitations of this approach is that its extension to imaging has required electro-optical or mechanical scanning of a scatter-sensing head over tissue, which is often time consuming, cumbersome, and hence is not suited for many clinical applications.

Illumination of tissue with structured light and extraction of absorption and diffuse scattering parameters was described by U.S. Pat. No. 8,509,879 to Durkin, and in US patent application 2010/021093 by Cuccia. In both Durkin and Cuccia, structured light is provided to tissue at at least 2 spatial frequencies and corresponding images are obtained. A voxel-based Monte-Carlo or diffusion model of light propagation having scattering and absorption parameters is typically constructed, and these parameters are extracted by fitting parameters of the model to provide a match of model-simulated light to light as measured in the images. This model-based interpretation is required because, at their choice of spatial frequencies (usually a low and high combination in the 0-0.3 $mm^{-1}$ range), the images they obtain are sensitive to both absorption and scattering properties of tissue. So their first processing step involves using a light-transport model to separate the absorption contribution from scattering contribution. These models make implicit assumptions about the underlying medium (tissue), which are often inaccurate in real world applications, particularly when interpreting superficial tissue structures.

The novel high frequency structured light imaging system and methodologies disclosed here overcomes these critical limitations and offers a fast, clinically compatible approach to diagnosing tissue-types during surgical procedures.

SUMMARY

A structured-light imaging system includes a structured light projector for illuminating a surface and an electronic camera configured to image the surface. An image processor receives the images and has structured light scatteroscopy (SLS) firmware with machine readable instructions that illuminate the surface with structured light having a spatial frequency of at least 0.5 $mm^{-1}$, and process the images to determine maps of scattering parameters of the surface independent of variations in absorption properties. In an embodiment, the system also has cameras configured to obtain a stereo pair of images of the surface, the image processor having 3D firmware for extracting a three dimensional surface model of the surface from the stereo pair of images and compensating the map for non-flat surfaces. In a particular embodiment, the surface is a surface of a biological tissue.

In an embodiment, a structured-light imaging system has apparatus configured to provide structured light to tissue; apparatus configured to produce images of tissue illuminated by the structured light; and an image processor coupled to receive the images. The image processor has a memory containing structured light scatteroscopy (SLS) firmware, the SLS firmware comprising machine readable instructions that, when executed, direct the processor to perform tasks including: using the apparatus configured to provide structured light, illuminating the tissue with structured light having a spatial frequency high enough to negate the effects of absorption, the structured light having a first phase, receiving images of tissue, advancing the structured light to at least a second phase, and processing the images to determine a map of scattering parameters at a surface of the tissue independent of variations in local absorption properties.

DETAILED DESCRIPTION OF THE EMBODIMENTS

This disclosure describes a new structured light imaging system optimized for tissue micromorphology imaging at multiple size scales, and its potential use in surgical guidance applications. This system is based on imaging with high spatial frequency structured light that enhances scattering contrast independent of local absorption changes in tissue, and offers direct and rapid imaging of morphology in superficial tissue layers.

The system allows imaging morphology variations at multiple size scales and sensitivity. In addition, the wavelength dependence of the scattering response is imaged to provide additional information, which could improve classification accuracy in diagnostic settings.

The system probes tissues with high spatial frequency structured light patterns to enhance sensitivity to the scattering contrast and simultaneously suppress sensitivity to absorption contrast. This offers a way to image tissue morphology changes directly without needing model-based interpretation to separate scattering effects from absorption effects. This technique's inherent insensitivity to absorption contrast is critical in surgical imaging applications where sensitivity to surface blood (hemoglobin) often masks useful information.

In an embodiment, this imaging approach requires the tissue specimens to be reasonably flat. Currently this limitation is overcome by placing the specimen on a glass plate and imaging in an inverted geometry. This approach works well for soft tissue imaging applications, such as in breast cancer margin assessment, where tissue surfaces conform well to the glass slides. Alternatively, a handheld probe version of this imaging hardware has a flat glass window at the distal tip. With this embodiment, the flat window is pressed onto tissue to ensure a flat imaging surface in in vivo imaging applications such as skin cancer diagnosis.

In an alternative embodiment, a three dimensional surface model is derived from stereo cameras and used to compensate for non-flat tissue.

Structured Light Imaging (SLI) imaging and spatial frequency domain imaging (SFDI)) is a reflectance-based wide-field imaging modality that works by illuminating a sample with light modulated according to spatially-varying amplitude basis functions, resulting in reflected light that contains information from different feature scales and sampling volumes. For example, the most straightforward type of basis function is a series of sinusoid projections of varying spatial frequencies. In SFDI the tissue response at each of the projection spatial frequencies is typically recovered by capturing observed images using a digital camera, then using a phase-based recovery technique. Spatial frequencies in the range of 0-0.3 mm$^{-1}$ are employed in SFDI. The reflectance response as a function of spatial frequency is then typically fit to an empirical voxel-based light diffusion model to extract the spatial maps of absorption and reduced scattering coefficients ($\mu_a$ and $\mu_s'$ respectively) of the imaged tissue specimen by fitting these parameters until modeled light matches the observed images. While this overcomes the limitations of point scanning, the recovered optical properties obtained using this spatial frequency range represent the bulk transport of light as deep as 8 mm in tissue, giving recovered absorption and scatter maps that are spatially blurred. Unfortunately, this blurring reduces the effectiveness of scattering texture analysis, which has been shown to have high discriminative value in separating benign and malignant tissue in previous studies.

To get around these limitations in our system we use a new imaging framework termed Structured Light Scatteroscopy (SLS), which is modified from SFDI and is optimized for direct measurement of the localized light scattering response in bulk tissues.

Figure 19:
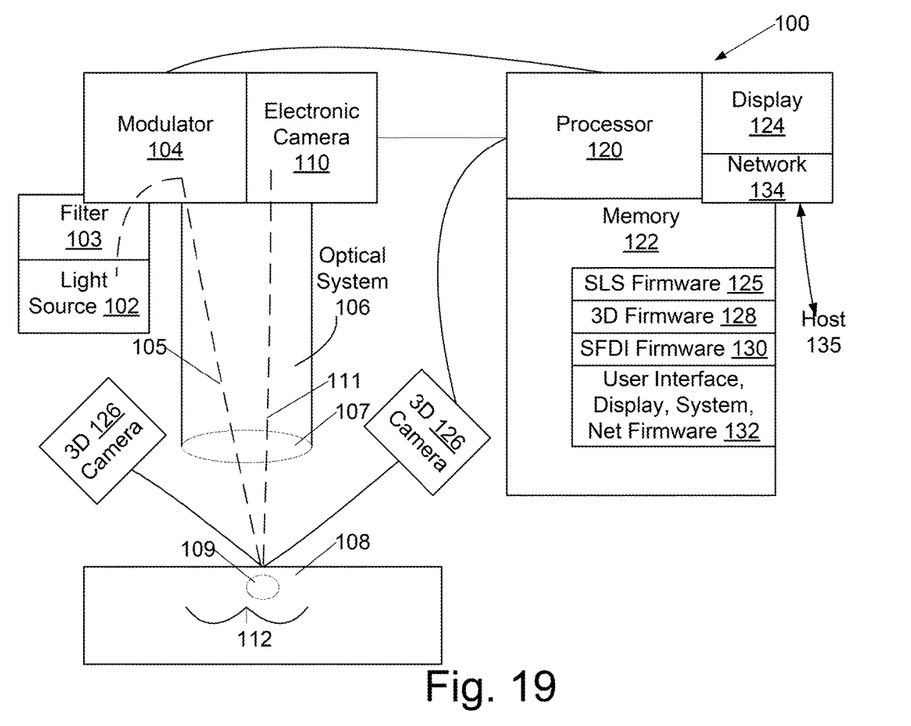
FIG. 19 is a block diagram of a structured-light scatteroscopy system.

The system has hardware illustrated in FIG. 19. In this system, a light source 102, which in embodiments is selected from an incandescent lamp, light-emitting diode lamps, or one or more lasers, provides light through a bandpass filter 103 to spatial modulator 104. Bandpass filter 103 is in an embodiment a filter-changer having multiple, switchable, filter elements adapted to provide multiple wavelengths of illumination light, and in another embodiment is a tunable filter. In particular embodiments, spatial modulator 104 is selected from a liquid crystal display or a digital micromirror projection display device (DMD), and operates under control of processor 120. In an alternative embodiment, spatial modulator 104 incorporates a rotary filter-changer having neutral-density striped patterns at predetermined spatial frequencies and phases, the filter-changer operates under control of processor 120. In another alternative embodiment the source 102 is a laser and the spatial modulator 104 is a fixed or replaceable diffractive optical element designed to produce specific structured light patterns.

Spatially modulated light 105 from modulator 104 passes through an optical system 106, including lens 107, onto tissue 108. Tissue 108 may include part or all of a tumor 109. Light from tissue 111 passes through a lens, which in some embodiments is the same lens 107 as used for illuminating tissue 108, and in other embodiments is a different lens, and other components of the optical system 106 into an electronic camera 110, which in an embodiment is a charge-coupled device (CCD) camera. In an alternative embodiment camera 110 is a standard Bayer-pattern complementary metal oxide semiconductor (CMOS) camera with a capability to image three wavelengths (or colors) simultaneously. Images from camera 110 are digitized and transmitted to processor 120 by an appropriate interface as known in the art of digital imaging. It should be noted that an area 112 of tissue 108 is illuminated with the modulated or patterned light 105 across a field on the tissue, not at a single point on the tissue, and camera 110 is configured to form an image of the illuminated area of tissue 108. SLS imaging firmware 125 is provided in memory 122. In a particular embodiment, an additional stereo-imaging pair of digital cameras 126 is provided for 3-D surface extraction, cameras 126 being adapted to provide digital images to processor 120, and 3-D surface extraction firmware 128 is provided in memory 122. In an alternate embodiment, camera 110 serves as one of the stereo-imaging cameras 126 in an appropriate geometrical configuration as known in the art of stereo imaging. Memory 122 also includes image display, user interface, and network firmware 132 so that system may communicate with, and save images to, a host 135, of which no details are shown.

Similar hardware to that in FIG. 19, with appropriate firmware, is also capable of performing structured-light imaging at other spatial frequencies, in an embodiment firmware is provided for both SFDI and SLS imaging. In this embodiment, SFDI firmware 130 is also provided in memory 122.

Figure 1:
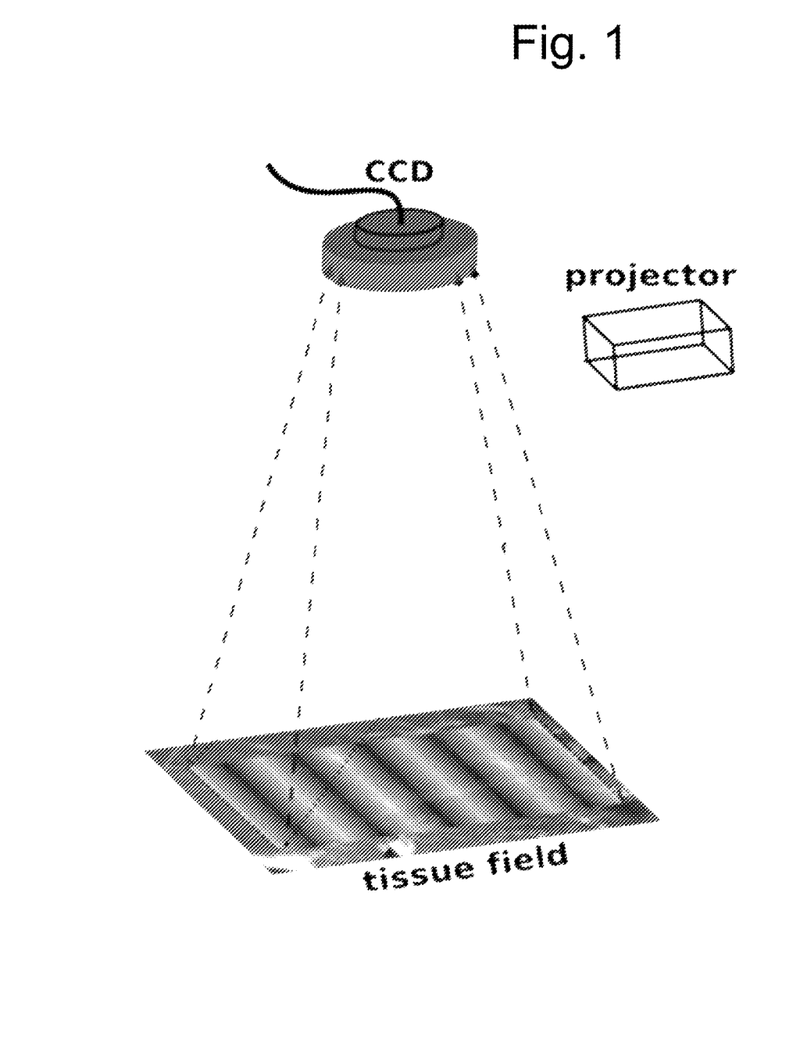
FIG. 1 is a simplified schematic of light paths produced by the system of FIG. 19, and as used for scatteroscopy.
Figure 2:
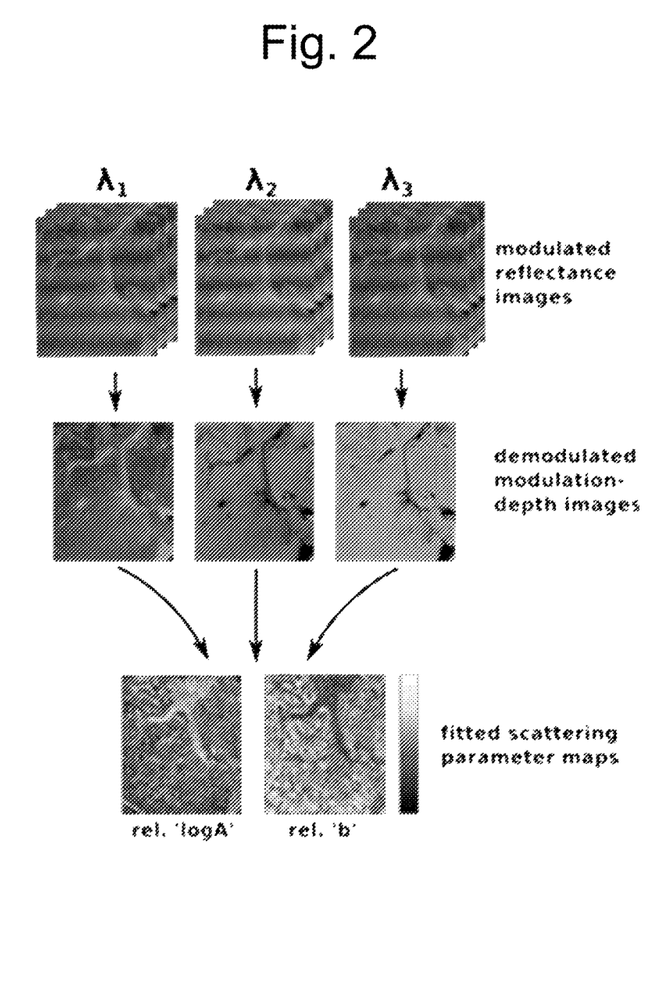
FIG. 2 is a data-flow diagram illustrating how images are processed by the system of FIG. 19.
Figure 3:
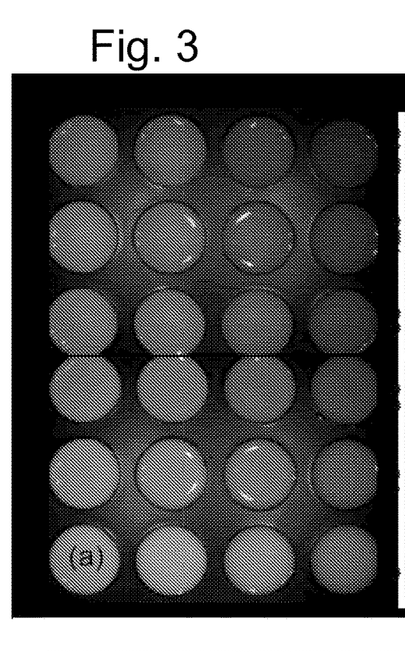
FIG. 3 is an illustration of a phantom used for validation of the scatteroscopy system.

In contrast to the traditional SFDI approach, the SLS technique samples the tissue response only at high spatial frequencies (typically greater than 0.5/mm). Separation of scattering and absorption signals is not achieved by light-propagation modeling, but by exploiting the fact that, at the limit of high spatial frequencies, the tissue response is insensitive to absorption variations and is very sensitive to scattering changes. This unique transport regime, therefore allows a direct way to extract scattering-sensitive signals without the need of a complex light transport models to separate the effects of absorption from those of scattering. The schematic of the SLS technique is shown in FIG. 1. In a particular prototype embodiment, we used a custom built structured light imaging system (Modulated Imaging Inc., Irvine, Calif.) to project and image a set of high spatial frequency sinusoid patterns, ranging from 0.5 $mm^{-1}$ to 1 $mm^{-1}$, over a rectangular field 112 of approximately 15 cm by 10 cm. FIG. 2 shows the data processing workflow performed by processor 120 executing an SLS image processing firmware 125 in memory 122 to process images captured by camera 110. At each spatial frequency, three different images were acquired with a phase offset of spatial modulation of illumination between each image (thereby acquiring at three phase offsets) to allow demodulation of the tissue response at the selected spatial frequency. Images at each phase offset were obtained at three different wavelength bands centered at 658 nm, 850 nm and 970 nm, using filter 103 to adjust illumination wavelength, in a sequential manner, to allow assessment of the wavelength dependence of the scatter response. For quantitative interpretation, all measurements are normalized to a spatially uniform reflectance standard. In an alternative embodiment, filters are used in camera 110 to provide wavelength selectivity. In alternative embodiments, additional phase offsets are used to permit rapid demodulation FIG. 3 is a photographic image of a portion of an Intralipid and Blood phantom matrix used for validating the system. The Intralipid concentration varies along each row from 4% to 0.5% and the blood concentrations vary along each column from 240 μM (micromolar) to 0 μM.

Figure 4:
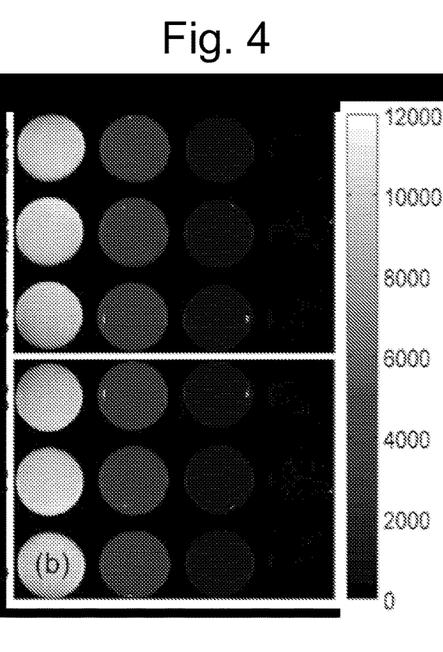
FIG. 4 is an illustration of demodulated reflectance image of the phantom matrix at 0.5 $mm^{-1}$ spatial frequency and 730 nm (nanometer) wavelength, showing negligible sensitivity to hemoglobin changes across the column.

FIG. 4 represents a demodulated reflectance image of the phantom matrix at 0.5 $mm^{-1}$ spatial frequency and 730 nm wavelength, showing negligible sensitivity to hemoglobin changes along columns, while providing significant sensitivity to intralipid concentration changes along each row.

Figure 5:
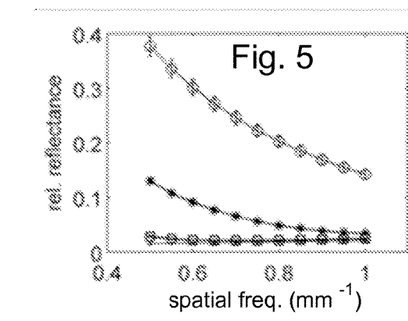
FIG. 5 is a plot of simulated reflectance versus spatial frequency.

FIG. 5 is a plot of simulated reflectance versus spatial frequency.

Figure 6:
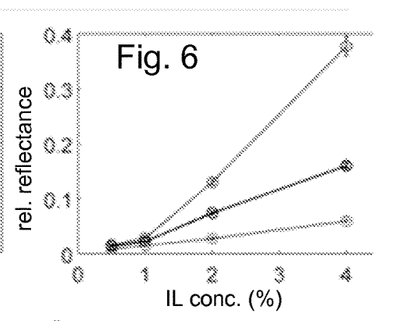
FIG. 6 is a plot of experimentally recovered reflectance versus intralipid concentration.

FIG. 6 is a plot of experimentally recovered reflectance versus Intralipid concentration, which is linearly proportional to the reduced scattering coefficient.

Figure 7:
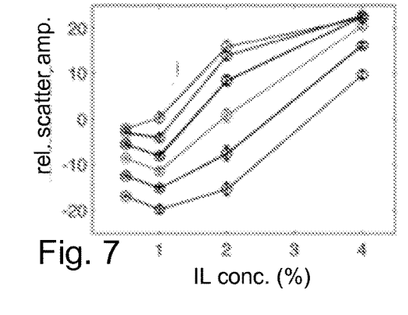
FIG. 7 is a plot of average relative scatter amplitude versus Intralipid concentration.

FIG. 7 is a plot of average relative scatter amplitude versus Intralipid concentration.

Figure 8:
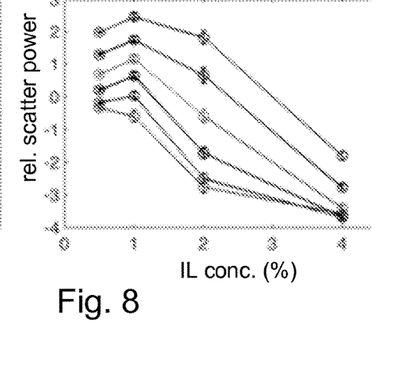
FIG. 8 is a plot of average relative scatter power versus Intralipid concentration

FIG. 8 is a plot of average relative scatter power versus Intralipid concentration. Standard deviation error bars in all plots represent variation due to change in background absorption.

While the spatial modulation frequency optimum for SLS is somewhat dependent on tissue type, we expect that SLS will perform best at spatial frequencies of 0.5 $mm^{-1}$ or greater, as shown by experiments on breast tissue. In general, we expect to image with a minimum spatial frequency that is high enough to negate the effects of absorption, allowing direct interpretation of scattering properties; in breast tissue this minimum frequency is approximately 0.5 $mm^{-1}$ but may differ for other tissue types or materials.

To evaluate the SLS signal's sensitivity to scattering changes and its apparent insensitivity to absorption changes, we imaged a set of Intralipid and blood phantoms with varying scattering and absorption properties as illustrated in FIGS. 3-4. Heparinized whole porcine blood (Lampire Biologicals) with a hematocrit value of 12.6 g/dL was used to prepare a matrix of Intralipid-Blood phantoms. Intralipid concentrations were fixed at 0.5%, 1%, 2 and 4% volume fraction of lipids, and the hemoglobin concentration in each case was varied from 0 μM to 240 μM. This range of intralipid concentrations are known to adequately cover the scattering properties of tissue and the absorption property range used here is approximately 10 times more than the typical average range observed in tissues. The phantom matrix was imaged at a set of high spatial frequencies in the range of 0.5 $mm^{-1}$ to 1 $mm^{-1}$ in 0.1 $mm^{-1}$ steps.

FIG. 3 shows the color photographic image of the phantom matrix, where the change in hemoglobin concentration across phantoms with fixed Intralipid concentration can be seen clearly. FIG. 4 shows the demodulated reflectance image acquired at a spatial frequency of 0.5 $mm^{-1}$ at 730 nm wavelength band, where it can be clearly seen that the recovered SLS image reflects only the scattering variations and are insensitive to absorption changes in the phantoms.

The reflectance response in this high spatial frequency range was also simulated using the Virtual Photonics Simulator platform. Optical properties in the range of $\mu_s'$ (reduced scattering coefficient)=0.5 to 4 $mm^{-1}$ and $\mu_a$ (absorption coefficient)=0 to 0.12 $mm^{-1}$ were used, approximately matching the range covered by the Intralipid-Blood phantoms. FIG. 5 shows the simulated reflectance values plotted as a function of spatial frequency for each of the considered $\mu_s'$ values and the standard deviation error bar captures the variation caused by the background absorption change within the full range given above. FIG. 4 shows the experimentally recovered average reflectance as a function of spatial frequency for each of the Intralipid concentrations imaged. The error bars capture the standard deviation of the recovered parameters caused by the background change in blood concentration. As expected, the SLS signal remains primarily sensitive to scattering changes and is largely independent of variations in local absorption both in simulations and the experiment. FIG. 5 shows the average reflectance at 0.5 $mm^{-1}$ spatial frequency as a function of Intralipid concentration, showing a linear relationship between the recovered reflectance and the scatter concentration, which is similar to the trend observed in other probe-based localized scatter response measurement studies. This linearity is lost at lower concentrations of Intralipid, understandably because the off-the-shelf, uncooled camera on the prototype SLS system was not sensitive enough to pick up the subtle change in the spatial frequency response at these low scattering levels—we expect linearity to lower levels with an improved camera system.

At each spatial frequency, the wavelength dependence of scatter response was obtained by fitting the multi-wavelength SLS data to an empirical model, $$R(\lambda)=A(\lambda)^{-b}$$ Equation 1.

FIGS. 6 and 7 show the relative scatter amplitude 'A' (shown as log(A)) and scatter power 'b' plotted as a function of intralipid concentration for a set of discrete spatial frequencies in the imaged 0.5 mm$^{-1}$ to 1 mm$^{-1}$ range. The spatial-frequency dependence of the extracted scattering parameters in these plots can be used to infer the multi-scale probing capabilities of SLS imaging. In localized scattering spectroscopy, it is well known that the recovered relative scatter parameters 'A' and 'b' vary with the probe size and the numerical aperture. This often results in varying scatter responses within the same medium when light is collected from different volumes of interrogation, due to differences in how the scattering PF is sampled, and provides a means to characterize ultrastructure variations in heterogeneous media, such as tissue, at multiple size scales. In SLS, the effective sampling volume decreases as the spatial frequency is increased, and thus varying the spatial frequencies provides a similar means to probe scatter property variations at multiple size scales. FIG. 6 captures this variation, where for a given concentration of intralipid, it can be seen that varying the spatial frequency alters the scattering response significantly.

Figure 9:
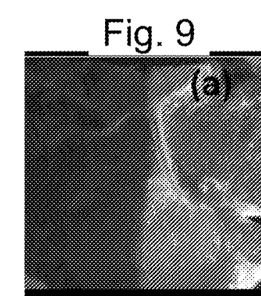
FIGS. 9, 10, 11, 12 and 13 are a series of photographic and corresponding SLS images obtained with the herein-described system of a bovine specimen coated with interfering blood, and described in more detail in text.
Figure 10:
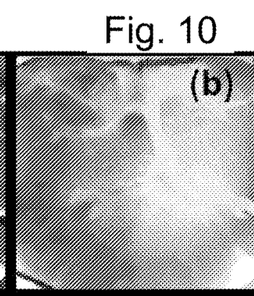
Figure 11:
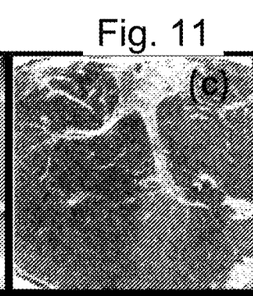
Figure 12:
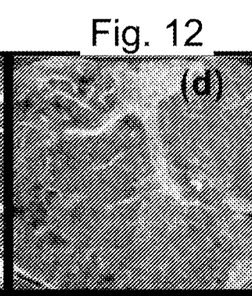
Figure 13:
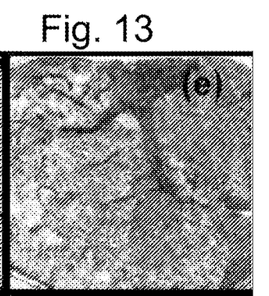
Figure 14:
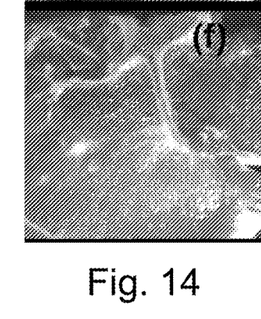
FIGS. 14, 15, 16, 17, and 18 are a series of photographic and corresponding SLS images obtained with the herein-described system of the bovine specimen of FIGS. 9-13 without the interfering blood.
Figure 15:
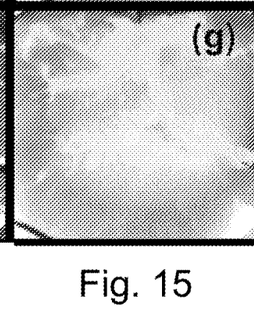
Figure 16:
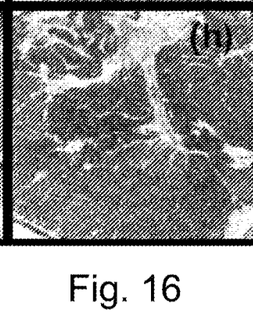
Figure 17:
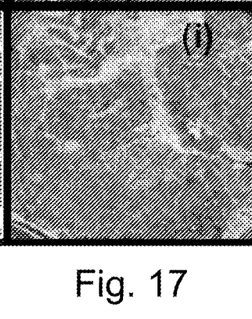
Figure 18:
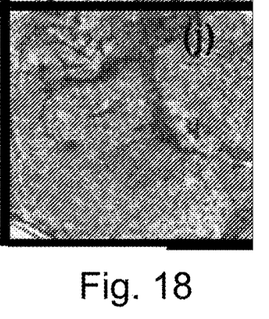

In FIGS. 9-18, images from particular specimens as illuminated and captured are provided. Row-wise, FIGS. 9, 10, 11, 12, and 13 are images are of a bovine tissue specimen where half of the imaging field was coated with a thick layer of whole blood and FIGS. 14, 15, 16, 17, 18 are images obtained of the same specimen imaged before coating with blood. Column-wise, FIGS. 9 and 14 are photographic images and FIGS. 10 and 15 are DC reflectance images at 852 nm. FIGS. 11 and 16 are demodulated reflectance images obtained with light spatially modulated at 0.5 mm$^{-1}$ at 852 nm wavelengths, and FIGS. 12 and 17 are a relative scatter amplitude log(A) image, and FIGS. 13 and 18 are a relative scatter power image 'b'. log(A) and b were obtained by fitting the SLS spectral images to Equation (1).

Finally, we demonstrate the advantage of SLS imaging in surgical settings by imaging bovine tissue specimen before and after coating its surface with whole blood. FIGS. 9, 10, 11, 12, and 13; show results from imaging the specimen before the specimen was coated with blood, and FIGS. 14, 15, 16, 17 and 18 before blood was applied. FIG. 9 show color photograph of the imaged specimen with one half of its surface coated with whole blood, where it can be seen that the contrast in the scattering features beneath the layer of whole blood is suppressed due to the light absorption by the whole blood layer. Reflectance images obtained using a uniform DC illumination at 852 nm wavelength is shown in FIGS. 10 and 15, despite hemoglobin's lower absorption at these wavelengths compared to the visible range, the images show a similar reduction in the scattering contrast. FIGS. 11 and 16 show the SLS reflectance image obtained at 0.5 mm−1 spatial frequency, at the same wavelength, where the contrast in scattering features appear clearly enhanced, even in the regions masked by the layer of whole blood. It must be noted that the amount of whole blood on the tissue surface reflects an extreme case, even in surgical specimens, but the SLS images still allow the recovery of scatter features in these conditions.

The wavelength dependence of scattering quantified by parameters 'logA' and 'b' are shown in FIGS. 12-13 and 17-18, respectively. Even though an SLS image acquired at a single wavelength is sufficient to visualize scatter features, the 'logA' and 'b' images derived from a spectral SLS scans are known to hold better diagnostic value compared to the single wavelength reflectance images. In a system that is expected to determine biologically interesting results, such as hemoglobin distribution maps, hemoglobin oxygenation maps, or tissue type information, we image at three wavelengths and post-process the images to determine ratios of scatter parameters at the two wavelengths at each pixel, and use these ratios to determine biologically interesting results from these ratios as well as the scatter parameters. In some embodiments, it is anticipated that more than two wavelengths will be used. In an alternate embodiment, Equation 1 may be replaced by a different mathematical model based on light transport characteristics of the target tissue or material.

In the current embodiment we illuminate and image the tissue surface with three or more phases of structured light to extract the demodulated response at each pixel of the tissue field. In an alternate embodiment this phase-based demodulation scheme is replaced with a Fourier-space method.

In conclusion, in SLS imaging, we image at high spatial frequencies and show that by choosing a minimum sampling frequency we can retrieve reflectance parameters that are directly dependent on scattering properties and are automatically independent of absorption. In theory we'd only need to image at one spatial frequency to recover the scattering related parameters. The downside is that with SLS imaging 1) we lose the ability to measure absorption using this technique, and 2) our measurements are very superficial—as they image several hundred microns into tissue as opposed to a few millimeters beneath tissue surface for SFDI.

But these issues may not pose significant hurdles in many applications where superficial imaging is sufficient and in cases where absorption-based contrast does not have reliable diagnostic value, such as diagnosis of superficial cancers and cancer imaging in surgical settings.

In real surgical settings, tissue is not always flat, and some tissue types resist deformation to a flat surface by application of a glass slide. In order to permit operation with non-flat tissue surfaces, processor 120 reads a stereo image pair from stereo digital cameras 126, and executes a 3-D surface extraction firmware 128 on the image pair to determine a model of the tissue surface. This tissue surface model, extracted from the 3D image pair, is used both to constrain the light transport model used for SFDI imaging, and to compensate for non-flat tissue in the SLS imaging above described.

Some differences between SFDI and SLS are summarized in the following table:

|  | SFDI | SLS |
| --- | --- | --- |
| Spatial Frequencies | Minimum 2 spatial frequencies needed, typically 1 low, 1 med. | Minimum 1 (high) spatial frequency needed |
| Typical Wavelengths | Minimum 2 wavelengths needed for extracting scatter parameters A & b (usually more required for scattering + absorption) | Minimum 2 wavelengths needed for extracting scatter parameters A & b. No absorption data is produced |
| Data recovery | Fit spatial frequency response R(f, λ) to a reflectance model (typically diffusion theory or MonteCarlo | No model-based interpretation is required to separate scattering and absorption contributions. SLS sampling offers inherent insensitivity |

-continued

| | SFDI | SLS |
|---|---|---|
| | simulations based) to separate scatter $S(\lambda)$ and absorption $Ab(\lambda)$ contributions | to absorption changes, so measurements directly reflect scattering contribution. i.e. $R(f, \lambda) = S(\lambda)$ |
| Postprocess for Physiological Properties | Measured $S(\lambda)$ is fit to another empirical model $S(\lambda) = A(\lambda)^{-b}$ to extract parameters A & b Ab($\lambda$) is fit using the Beer's law model to extract Hemoglobin content, oxygen saturation, lipid concentration etc. | Measured $S(\lambda)$ is fit to another empirical model $S(\lambda) = A(\lambda)^{-b}$ to extract parameters 'relative' A & b. Note that 'relative' A & b are not same as A & b extracted in SFDI, but both are still purely scattering related metrics. We have shown in previous studies that 'relative' A & b parameters are diagnostically useful in detecting cancers in excised breast specimens. Under certain situations where the empirical model above is not accurate, the tissue scattering response at a single or a plurality of wavelengths may be directly interpreted for diagnosis. |
| Depth in Tissue | Larger volume of tissue is sampled in the depth direction, typically several mm. | Very superficial sampling, typically <1 mm |

In an embodiment, the scattering parameters and maps of determined biologically interesting properties are further processed by an automatic tissue classifier to determine a map of tissue type. In an alternate embodiment the measured scattered reflectance at individual wavelengths is directly interpreted using appropriate classification frameworks without parameterization using empirical scattering models.

The term firmware as used herein includes a sequence of machine readable instructions that, when executed, performs a function as herein described. Firmware may be contained within a read-only memory, or loaded into and executed from a random access memory. A memory as herein described may include any or all of random access memory, read only or programmable read only memory, flash memory, and disk memory systems as known in the art of computing systems.

While the following discussion, and experiments are focused on imaging systems for biological tissues (including living human and animal tissues as well as dead tissues such as meat), it is anticipated that the system and method herein described are applicable to other materials. For example, the system may be of use in imaging surface coatings, such as latex, oil, or epoxy paints, or plastic coatings including those applied by dipping or spraying. As another example, we anticipate that the system is of use in monitoring material quality in a production line for translucent or scattering materials, such as a web of damp paper formed on a Fourdriner or similar machine as it passes to a dryer, or of translucent plastic extrusions. Similarly, the system may be of use in examining surfaces of objects fabricated from such translucent or scattering materials for non-uniformities or damage.

Figure 20:
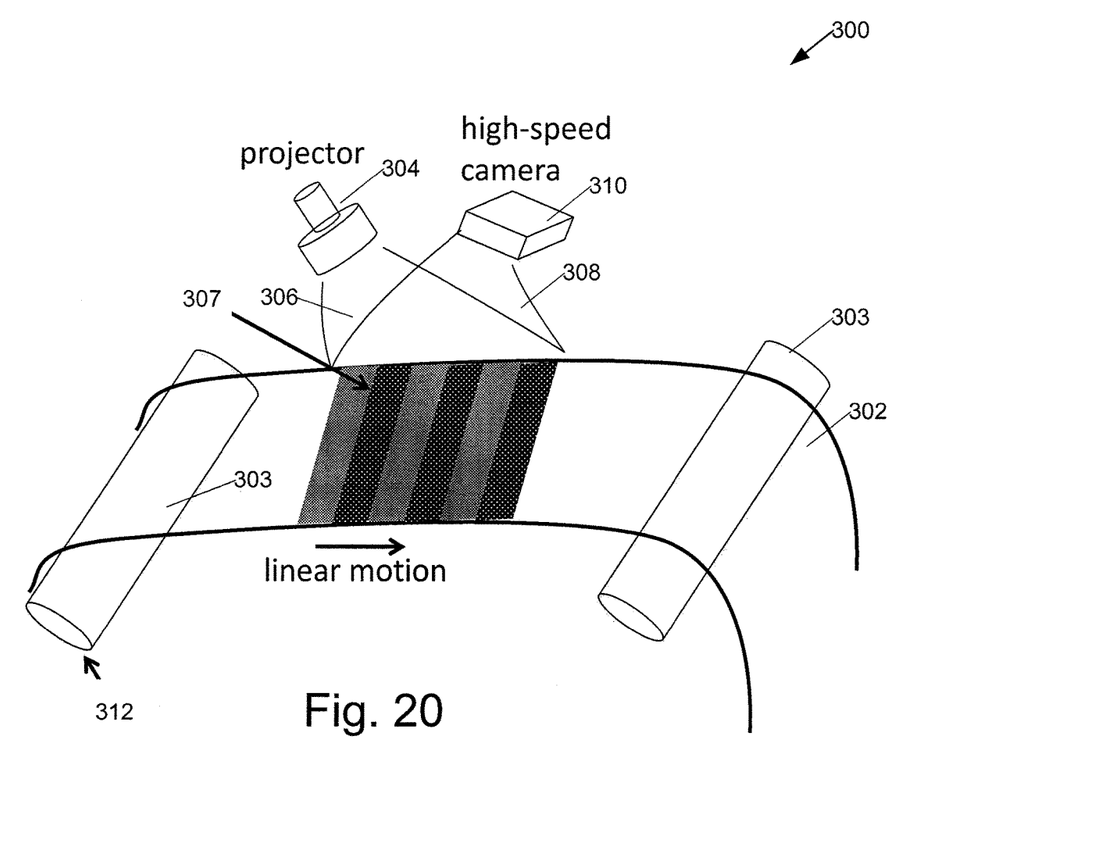
FIG. 20 is an illustration of use of a single structured-light pattern and camera to provide three-phase information for image reconstruction.

In some production monitoring systems 300, as illustrated in FIG. 20, where a continuous web or sheet 302 of material is produced and passes over rollers 303, a projector 304 adapted to provide a fixed structured-light pattern of one or more desired wavelengths is used to project structured light 306 onto a surface of the material, where light 306 forms a structured illumination 307 on the surface. Light 308 reflected and scattered by the material is captured by a camera 310. As the material moves over the rollers 303, an encoder at one or more rollers may be used to measure movement of the material sheet 302 and determine three times associated with three positions of the material—each position of the material corresponds to one of the three phases described above with reference to stationary materials such as biological tissues. Images are captured by camera 310 at each of the three times, the resulting three images are used to reconstruct scatter-based images of the surface of the material, which may then be viewed by a human or processed by an image processor similar to that of FIG. 1 to determine flaw locations or to monitor material quality.

For purposes of this document, a translucent material is a material that permits at least some incident light to penetrate into the material, and where the material contains inclusions or non-uniformities that scatter light. Such materials include biological tissues, as well as many white plastics and paints.

Combinations

The various features and concepts described herein can be found in many different combinations in a particular system or method. Among those combinations anticipated are A structured-light imaging system designated A including apparatus configured to provide structured light to tissue surface; apparatus configured to produce images of a surface illuminated by the structured light; and an image processor coupled to receive the images. The image processor has a memory containing structured light scatteroscopy (SLS) firmware, the SLS firmware comprising machine readable instructions that, when executed, direct the processor to perform tasks including: using the apparatus configured to provide structured light, illuminating the surface with structured light having a spatial frequency high enough to negate the effects of absorption, the structured light having a first phase, receiving images of the surface, advancing the structured light to at least a second phase, and processing the images to determine a map of scattering parameters of the surface independent of the variations in surface absorption properties. A structured-light imaging system designated AA including the system designated A wherein the firmware comprises machine readable instructions that, when executed, direct the processor to perform tasks including advancing the structured light to at least a third phase, and repeating the illuminating the surface and receiving and images of surface.

A structured-light imaging system designated AAA including the system designated A or AA wherein the surface is a surface of a biological tissue.

A structured-light imaging system designated AB including the system designated AAA, A or AA wherein the spatial frequency of the structured light is at least 0.5 mm−1.

A structured-light imaging system designated AC including the system designated AAA, A, AB, or AA wherein the processing of images uses at least a phase-based demodulation technique.

A structured-light imaging system designated AD including the system designated AAA, A, AB, or AA wherein the processing of images includes a Fourier space demodulation technique.

A structured-light imaging system designated AE including the system designated AAA, AB, AC, AD, or AA further comprising at least a second camera, the cameras being configured to obtain a stereo pair of images of tissue, the image processor further configured with 3D firmware comprising machine readable instructions for extracting a three dimensional surface model of the tissue from the stereo pair of images, and for using the three dimensional surface model of the tissue during the processing of images.

A structured-light imaging system designated AF including the system designated A, AB, AC, AD, AE, or AA wherein the apparatus configured to provide structured light comprises a digital micro-mirror device.

A structured-light imaging system designated AG including the system designated A, AB, AC, AD, AE, AF, or AA wherein the apparatus configured to provide structured light is configured to provide structured light at a first wavelength, and at at least a second wavelength in sequence, and wherein the image processor is configured to acquire images at each of the first and second wavelength.

A structured-light imaging system designated AH including the system designated AAA, A, AB, AC, AD, AE, AF, AG, or AA further including spatial frequency domain imaging (SFDI) firmware, the SFDI firmware comprising machine readable instructions that, when executed, cause the processor to: construct a voxel based model having attenuation and scattering parameters, the model configured according to the three dimensional surface model; illuminate tissue with structured light patterned at least two spatial frequencies in the 0 to 0.3 mm−1 range; receive images of the surface; and fit the attenuation and scattering parameters to the received images.

A method of imaging tissue designated B includes: providing structured light to a surface, the structured light having a spatial frequency high enough to negate the effects of absorption, the structure light having a first phase; acquiring images of the surface illuminated by the structured light; receiving the images into an image processor; advancing the structured light to at least a second phase, and repeating the providing structured light to the surface and receiving images of the surface; and processing the images to determine a map of scattering parameters of the surface.

A method of imaging a surface designated BA including the method designated B and further including advancing the structured light to at least a third phase, and repeating the providing of light to the surface, acquiring images of the surface, and receiving images into the image processor.

A method of imaging a surface designated BB including the method designated B or BA and further including wherein the spatial frequency of the structured light is at least 0.5 mm−1.

A method of imaging a surface designated BC including the method designated B, BA or BB wherein the processing of images of the surface uses a phase-based demodulation technique.

A method of imaging tissue designated BD including the method designated B, BA or BB wherein the processing of images of the surface includes a Fourier space reconstruction.

A method of imaging a surface designated BE including the method designated B, BA, BB, BC, or BD wherein the apparatus configured to provide structured light comprises a digital micro-mirror device.

A method of imaging a surface designated BF including the method designated B, BA, BB, BC, BD, or BE wherein the apparatus configured to provide structured light is configured to provide structured light at a first wavelength, and at at least a second wavelength in sequence.

A method of imaging a surface designated BG including the method designated B, BA, BB, BC, BD, BE or BF further including spatial frequency domain imaging (SFDI) including: constructing a voxel based model having attenuation and scattering parameters, the model configured according to the three dimensional surface model; illuminating tissue with structured light patterned at least two spatial frequencies in the 0 to 0.3 mm−1 range; receiving images of the surface; and fitting the attenuation and scattering parameters to the received images.

The method of imaging a surface designated B, BA, BB, BC, BD, BD, BF, or BG wherein the surface is a surface of a biological tissue.

Changes may be made in the above methods and systems without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:

1. A structured-light in surgery imaging system comprising:
   apparatus configured to provide structured light to tissue;
   apparatus configured to produce images of tissue illuminated by the structured light;
   an image processor coupled to receive the images with a first camera;
   the image processor having a memory containing structured light scatteroscopy (SLS) firmware, the SLS firmware comprising machine readable instructions that, when executed, direct the processor to perform tasks including:
   obtaining a stereo pair of images;
   extracting a three dimensional surface model of the tissue from the stereo pair of images;
   using the apparatus configured to provide structured light to illuminate the tissue with structured light having a spatial frequency high enough to negate the effects of absorption, the structured light having a first phase,
   receiving images of tissue;
   advancing the structured light to at least a second phase, and repeat using the apparatus configured to provide structured light to illuminate the tissue and receiving images of tissue;
   and processing the images to determine a map of scattering parameters at a surface of the tissue, the machine-readable instructions for determining a map of scattering parameters configured to ignore attenuation, and to use the three dimensional surface model of the tissue to constrain the map of scattering parameters;
   advancing the structured light to at least a third phase, and repeating the illuminating the tissue and receiving and processing images of tissue.

2. The system of claim 1 wherein the firmware comprises machine readable instructions that, when executed, direct the processor to perform tasks including advancing the structured light to at least a fourth phase, and repeating the illuminating the tissue and receiving and images of tissue.

3. The system of claim 2 wherein the spatial frequency of the structured light is at least 0.5 mm−1.

4. The system of claim 1 wherein the processing of images of tissue uses at least a phase-based demodulation technique.

5. The system of claim 1 wherein the processing of images of tissue includes a Fourier space demodulation technique.

6. The system of claim 1 wherein the apparatus configured to provide structured light comprises a digital micro-mirror device.

7. The system of claim 6 wherein the apparatus configured to provide structured light is configured to provide structured light at a first wavelength, and at least a second wavelength, in sequence.

8. The system of claim 1 further comprising spatial frequency domain imaging (SFDI) firmware, the SFDI firmware comprising machine readable instructions that, when executed, cause the processor to:
construct a voxel based model having attenuation and scattering parameters, the model configured according to the three dimensional surface model;
illuminate tissue with structured light patterned at least two spatial frequencies in the 0 to 0.3 $mm^{-1}$ range;
receive images of tissue; and
fit the attenuation and scattering parameters to the received images.

9. A method of imaging a surface during surgery comprising:
providing structured light at a first wavelength, and at least a second wavelength in sequence to the surface, the structured light having a spatial frequency high enough to negate the effects of absorption, the structure light having a first phase;
acquiring images of surface illuminated by the structured light at the first and second wavelengths;
receiving the images into an image processor;
advancing the structured light to at least a second phase, and repeating the providing structured light to the surface and receiving images of the surface;
processing the images to determine a map of scattering parameters at the surface; and
processing the images to map fluorophore concentration in three dimensions beneath the surface.

10. The method of claim 9 further comprising advancing the structured light to at least a third phase, and repeating the providing of light to the surface, acquiring images of the surface, and receiving images into the image processor.

11. The method of claim 10 wherein the spatial frequency of the structured light is at least 0.5 mm−1.

12. The method of claim 11 wherein the processing of images of the surface uses a phase-based demodulation technique.

13. The method of claim 11 wherein the processing of images of the surface includes a Fourier space reconstruction.

14. The method of claim 9, wherein the apparatus configured to provide structured light comprises a digital micromirror device.

15. The method of claim 9, further comprising spatial frequency domain imaging (SFDI) comprising:
constructing a voxel based model having attenuation and scattering parameters at each of a plurality of voxels, the model configured according to the three dimensional surface model;
illuminating tissue with structured light patterned at least two spatial frequencies in the 0 to 0.3 mm−1 range;
receiving images of the surface; and
fitting the attenuation and scattering parameters to the received images.

16. The method of claim 9 further comprising obtaining a stereo pair of images, extracting a three dimensional surface model from the stereo pair of images, and constraining the step of processing the images with the three dimensional surface model.

* * * * *